United States Patent [19]

Gianezio et al.

[11] Patent Number: 4,520,511
[45] Date of Patent: Jun. 4, 1985

[54] HIP PROSTHESIS WITH EXPANDING FEMORAL COMPONENT

[76] Inventors: Paribelli Gianezio, Via Branzanti 2; Godoli Nunzio, Via Boccaccini, both of Ravenna, Italy

[21] Appl. No.: 403,419

[22] Filed: Jul. 30, 1982

[51] Int. Cl.³ .............................................. A61F 1/24
[52] U.S. Cl. ................................ 3/1.913; 128/92 CA; 128/92 BC
[58] Field of Search .......................... 3/1.9, 1.91, 1.912, 3/1.913; 128/92 C, 92 CA, 92 B, 92 BA, 92 BB, 92 BC

[56] References Cited

U.S. PATENT DOCUMENTS

| | | | |
|---|---|---|---|
| 2,719,522 | 10/1955 | Hudack | 3/1.913 X |
| 3,805,302 | 4/1974 | Mathys | 128/92 C X |
| 3,846,846 | 11/1974 | Fischer | 3/1.913 |
| 4,091,806 | 5/1978 | Aginsky | 128/92 BC |
| 4,115,875 | 9/1978 | Rambert et al. | 128/92 CA |
| 4,167,047 | 9/1979 | Grundei et al. | 128/92 C X |

FOREIGN PATENT DOCUMENTS

| | | | |
|---|---|---|---|
| 0017743 | 10/1980 | European Pat. Off. | 3/1.913 |
| 2359644 | 7/1975 | Fed. Rep. of Germany | 128/92 BC |

*Primary Examiner*—Ronald L. Frinks
*Attorney, Agent, or Firm*—McAulay, Fields, Fisher, Goldstein & Nissen

[57] ABSTRACT

A hip prosthesis adapted to be fixed in the femoral articulation, with gradual expansion against the wall of the femoral canal by means of a screw, has a top part shaped with a seat for settling the nut of a screw in a lower part which has three outwardly biased longitudinal sectors which are internally threaded and held together by the screw. After insertion, unscrewing causes the progressive separation of the three expansion sectors which locks the prosthesis in the femoral or thighbone canal. The attachment is strengthened by external circular retaining ridges on the sectors.

14 Claims, 2 Drawing Figures

HIP PROSTHESIS WITH EXPANDING FEMORAL COMPONENT

FIELD OF THE INVENTION

This invention refers to a hip prosthesis to be fixed in the femoral joint, which has a uniform expansion and can be adjusted on the inner wall of a cavity by means of a screw acting on the expandable part.

Following arthrosis, ischemic problems of the head, neck fracture or joint tumors, it often becomes necessary to replace the coxofermoral articulation, either partially or totally, with a prosthesis. For fixing it, several systems are used at present.

One system employs acrylic quick setting cement which has an intense exothermic reaction. This system may become inefficient due to tissue necrosis and give rise to problems of various kinds on account of the reaction of the organism to cement, such as blood pressure lowering, psychological problems and collapse syndromes.

Another system involves boring the femoral duct and fixing the prosthesis in the bore by a screw. With this system the prosthesis unscrews with the passage of time and moves from its proper position.

The system of this invention solves the above problem by excluding the use of an interposed member and by fitting the prosthesis in the femoral canal by implanting in it an expanding device which operates with adjustable pressure and uniform expansion. This system allows integrally fitting the prosthesis to the skeleton thus avoiding the use of parts which are differently stressed while minimizing the chances of rejection by the organism.

In particular, the elimination of the bonding material helps to avoid complication, if the prosthesis must be replaced by having to remove the cement from the articulation, or by the weakening of the femoral cortical, or because of tissues degenerated by the cement.

SUMMARY OF THE INVENTION

The invention provides a hip prosthesis comprising an elongated metallic member adapted for insertion in the femoral canal against the inner surface of the large femoral trocanter and which has a slanted upper end terminating in an articulation; the upper end being formed with a retaining collar adapted to rest against the median counterfort of the femur; the lower end of the member having a plurality of longitudinal slits defining expansible, outwardly biased resilient sectors adapted to grip the inner surface of the femoral trocanther; and a longitudinal rod and actuating means in the rod for expanding the sectors after insertion of the prosthesis in the femoral canal.

DISCLOSURE OF BEST MODE OF THE INVENTION

Figures 1, 2:
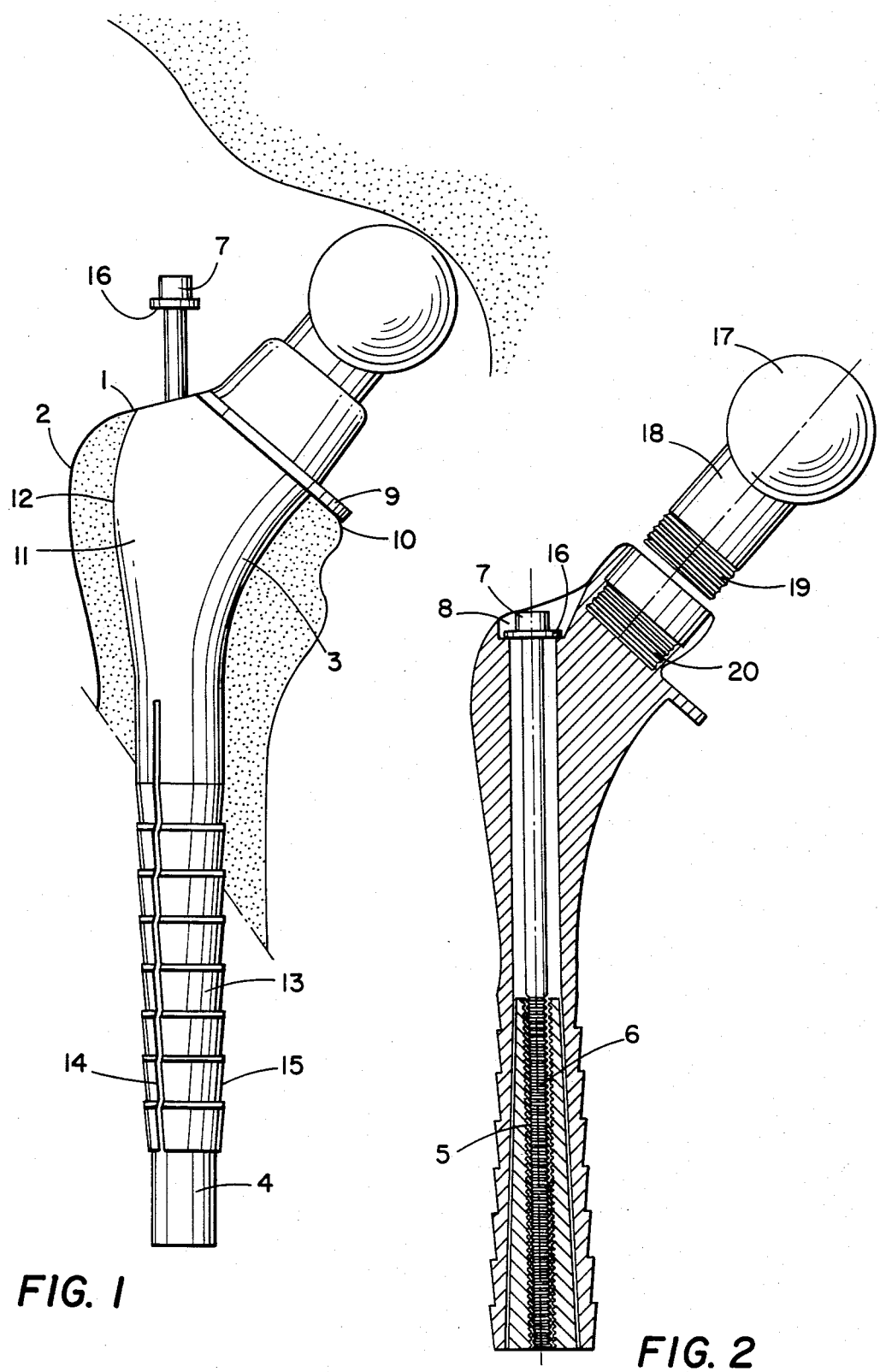
FIG. 1 illustrates in non-limiting fashion a preferred embodiment of the invention wherein the prosthesis is shown in front elevational view with its radial sectors expanded.
FIG. 2 is a longitudinal section of the same with its sectors expanded.

This embodiment involves the introduction of the metal or plastic part 3 into cavity 1 of the femoral joint 2. Metal or plastic part 3 has a cone-shaped rod 4 with a lower truncated end. Inside rod 4 is a threaded bore 5 to which is screwed screw 6 operated by a nut 7 fitting in seat 8 which allows lifting part 4. Part 3 can be stabilized on the joint by means of a biased collar 9 which rests on the middle counterfort of the thigh bone 10, while enlarged median part 11 is set in contact with the inside surface 12 of the large femoral trocanther. The cylindrical bottom part 13 has three outwardly biased, resilient longitudinal spaced sectors which expand as part 4 ascends. On the outer wall, part 13 has a system of uninterrupted shoulders 15 to increase its gripping effect. To secure in place, the prosthesis is at first fitted in the femoral canal, and the sectors 14 are expanded by unscrewing screw 6 by acting on the control nut 7 bound in its seat and rotation its circular base 16 only, in seat 8. The prosthesis can be completed with ball 17 on the cylindrical rod 18 threaded by its end 19 in coaxial seat 20.

The components, the control means of the screw, and the shape and number of the expanding sectors can be varied as desired as can the materials of construction which may be replaced by others suited for the purpose. In particular, the spherical head can be otherwise fitted through a notch or channel system.

The prosthesis of the invention can be manufactured by any technique well known in the art from any alloys used in prosthetic devices. Similarly, any suitable, inert, plastic material which is body compatible can be used.

It will be evident that many modifications of the present invention will become apparent to those skilled in the art once the concept thereof is understood.

What is claimed is:

1. A hip prosthesis comprising:
   an elongated member adapted for insertion in the femoral canal against the inner surface of the large femoral trocanter having a longitudinal bore and a slanted upper end terminating in an articulation;
   said upper end being formed with a retaining collar adapted to rest against the median counterfort of the femur;
   the lower end of the member having a plurality of longitudinal slits defining a plurality of expansible, resilient, unitary, straight, sectors adapted to grip the inner surface of the femoral trocanther;
   a longitudinal, internally threaded rod with said bore; and,
   actuating means in said rod for expanding said sectors after insertion of the prosthesis in said femoral canal;
   said sectors having spaced outwardly extending, peripheral shoulders for locking said prosthesis in place.

2. The prosthesis of claim 1, wherein said rod is conical and has a truncated lower end adapted to radially expand said sectors upon being raised by said actuating means.

3. The prosthesis of claim 1, wherein said actuating means is a screw fitting in said bore and threaded in said rod.

4. The prosthesis of claim 3, wherein said member has a seat in the upper part thereof at the end of said bore and said screw has a head received in said seat.

5. The prosthesis of claim 1, wherein said member has an enlarged median part fitting against the inner surface of the femoral large trocanter.

6. The prosthesis of claim 1, wherein said member has three longitudinal sectors; said sectors being expanded by the upward displacement of said actuating means.

7. The prosthesis of claim 4, wherein said seat is generally circular.

8. The prothesis of claim 1, wherein said articulation comprises a ball at the upper end of a rod threaded at its lower end, said member having a threaded seat above said retaining collar and receiving said threaded end of said rod.

9. The prosthesis of claim 1, wherein said member is metallic.

10. The prothesis of claim 1, wherein said member is formed of inert plastic material acceptable to the organism.

11. The prosthesis of claim 3, wherein said rod is conical and has a truncated lower end adapted to radically expand said sectors upon being raised by said actuating means.

12. The prosthesis of claim 11, wherein said member has an enlarged median part fitting against the inner surface of the femoral large trocanter, and three longitudinal sectors, said sectors being expanded by the upward displacement of said actuating means.

13. The prosthesis of claim 4, wherein said member has a generally circular seat in the upper part thereof.

14. The prosthesis of claim 13, wherein said member is formed of inert plastic material acceptable to the organism.

* * * * *